United States Patent [19]

Yamakoshi

[11] 4,204,545
[45] May 27, 1980

[54] LIMB BLOOD FLOWMETER

[75] Inventor: Kenichi Yamakoshi, Tokyo, Japan

[73] Assignee: Asahi Medical Co., Ltd., Tokyo, Japan

[21] Appl. No.: 898,561

[22] Filed: Apr. 21, 1978

[30] Foreign Application Priority Data

Sep. 7, 1977 [JP] Japan .................... 52-107441

[51] Int. Cl.² .............................................. A61B 5/02
[52] U.S. Cl. .................................. 128/693; 128/689; 128/680
[58] Field of Search .......... 128/2.05 V, 2.1 Z, 2.05 F, 128/680, 689, 691, 693, 734; 73/194 R

[56] References Cited

U.S. PATENT DOCUMENTS

| | | | |
|---|---|---|---|
| 3,457,909 | 7/1969 | Laird | 128/2.05 A |
| 3,835,839 | 9/1974 | Brown | 128/2.05 F |
| 3,835,840 | 9/1974 | Mount | 128/2.05 F |
| 3,874,368 | 4/1975 | Asrican | 128/2.1 Z |
| 3,958,577 | 5/1976 | Rodler | 128/420 A |
| 3,994,284 | 11/1976 | Voelker | 128/2.1 Z X |
| 3,996,924 | 12/1976 | Wheeler | 128/2.1 Z |
| 3,996,925 | 12/1976 | Djordjevich | 128/2.1 Z X |

OTHER PUBLICATIONS

Kubicek, W. G. et al., "The Minnesota Impedance Cardiograph Theory and Applications," *Biomed. Engr.*, vol. 9, No. 9, Sep., 1974, pp. 410–416.

Darling, R. C. et al., "Quantitative Segmental Pulse Volume Recorder," *Surgery*, Dec., 1972, vol. 72, No. 6, pp. 873–887.

Hokanson, D. E. et al., "An Electrically Calibrated Plethysmograph for Direct Measurement of Limb Blood Flow," IEEE Transactions on Biomed. Engr., vol. BME-22, No. 1, pp. 25–29, Jan., 1975.

Primary Examiner—Robert W. Michell
Assistant Examiner—Francis J. Jaworski
Attorney, Agent, or Firm—Pollock, Vande Sande and Priddy

[57] ABSTRACT

A human limb to be examined is pressurized on the side of the heart to occlude the venous return alone for the measurement of admittance of the limb, and the measured initial admittance is retained and compared with subsequently measured admittance to detect a difference $\Delta Y$ therebetween. The blood resistivity $\rho$, the length $L$ of the limb segment to be examined and its tissue volume $V_O$ are respectively set, and $\rho L^2 \Delta Y / V_O$ is computated. The initial gradient of the computation result to time is indicative of the blood flow rate in the limb being examined.

13 Claims, 13 Drawing Figures

LIMB BLOOD FLOWMETER

BACKGROUND OF THE INVENTION

This invention relates to a limb blood flowmeter for measuring the blood flow rate in human limb segments.

For example, in the case of using an artificial kidney, the blood is dialyzed by a hemodialyzer. In such a case, the measurement of the blood flow rate is indispensable to the determination of the period time for hemodialysis, that is, the time for each application of blood of substantially the whole body to the hemodialyzer. One method that has usually been employed in conventional hemodialyzers for the measurement of the blood flow rate is to make transparent a blood flow path between the hemodialyzer and the human body, form a bubble in the path at a certain place and measure the time for the passage of the bubble for a predetermined distance in the path, thereby to measure the blood flow rate. However, such a method is very troublesome, and the bubble in the blood entails a danger to the patient and, on top of that, the measurement obtained is relatively inaccurate.

In view of the abovesaid defects, there is a strong demand for means for accurately measuring the blood flow rate in the human body by a non-invasive method. One method for measuring blood flow rate or blood volume change non-invasively is the venous occlusion method. With this method, an occluding pressure cuff is wrapped around a limb such as an arm or leg to occlude the venous return and hence cause an increase in the tissue volume in the limb by the arterial inflow, and the increased tissue volume is measured to detect the blood flow rate. Thus the blood flow rate can be measured non-invasively without taking out a blood vessel for directly measuring the blood flow rate. This measurement is carried out in the following manner:- For example, an arm is immersed in water or like liquid contained in a measuring chamber, and the venous return is stopped, with the arm and the chamber held liquid-tight therebetween. An increase in the tissue volume of the arm by the arterial inflow is detected from the quantity of liquid which is caused to overflow by the arterial inflow, and then the blood volume flow is measured from the amount of tissue volume thus increased. However, a change in condition of the human limb due to the liquid temperature change during the measurement introduces an error in measurement. Accordingly the liquid temperature must be kept constant, and its control is complicated and, further, when the arm is immersed in the liquid for a long period of time, as mentioned above, the blood flow rate cannot be measured repeatedly and continuously.

A method that has been proposed for measurement of the ventricular stroke volume by measuring impedance changes based on ventricular systol is impedance plethysmography. This is set forth, for instance, in Medical Physics, Vol. II, Year Book 736/743 (1950), J. Nyboer, "Plethysmograph: Impedance", Aerospace Med. Vol. 37, 1208/1212 (1966), W. G. Kubicek et al, "Development and Evaluation of an Impedance Cardiac Output System" and so on. This method is to supply a high-frequency, very small current to a limb segment and measure the limb blood flow from a change in the electrical impedance of the limb segment caused by the venous occlusion. This method enables non-invasive and continuous measurement of the blood flow, but the impedance variation by a change in the blood volume is affected by the initial impedance value of the segment to be examined and does not coincide accurately with the actual change in the volume. Consequently the impedance variation is measured inclusive of the electrical characteristics of other tissues than that of the region desired to be examined, therefore the abovesaid method is defective in theory and in the accuracy of measurement.

Further, in his thesis submitted to the Faculty of the Graduate School of the University of Minnesota, 1965, "Cardiac Output Determinations Using Impedance Plethysmography", R. P. Patterson made a theoretical proposal of utilizing admittance for measuring the ventricular stroke volume.

An object of this invention is to provide a limb blood flowmeter which enables non-invasive, continuous and accurate measurement of the limb blood flow rate.

Another object of this invention is to provide a limb blood flowmeter which enables accurate measurement of the limb blood flow rate regardless of the initial admittance value of the limb and without including the electrical characteristics of other tissues than that of the region to be examined.

Still another object of this invention is to provide a limb blood flowmeter using the admittance method which is capable of direct measurement of a change in the blood volume independently of the initial admittance value of the limb to be examined.

SUMMARY OF THE INVENTION

In accordance with this invention, the venous return in the limb to be examined is occluded, and the initial admittance value of the limb is measured and held and is then compared with the subsequent admittance value of the limb due to the venous occlusion to obtain the difference $\Delta Y$ between them. The blood resistivity $\rho$, the length L of the segment to be examined and its volume $V_O$ are respectively set in setters, and $\rho L^2 \Delta Y / V_O$ is computated, and then the computation result is recorded on an output device. A series of operations for the venous occlusion, the holding of the initial admittance and the drive of the recorder are sequentially carried out under the control of a controller. Thus the blood flow rate can be obtained from the initial gradient of a plethysmogram recorded on the recorder to time. In the above calculation, $\rho$, $L^2$ and $V_O$ are constants and thus it is obvious that the blood volume change is directly proportional to the difference $\Delta Y$ alone.

DESCRIPTION OF THE PREFERRED EMBODIMENTS

Figure 1:
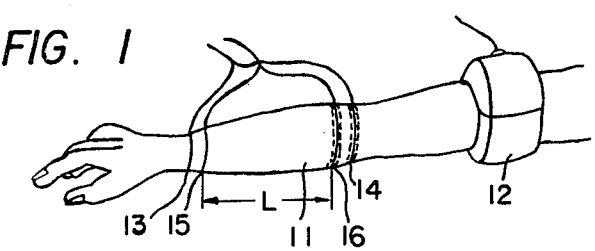
FIG. 1 shows a schematic diagram of the four electrodes method and the position of the pneumatic cuff for venous occlusion in a human limb.

In measurement of the limb blood flow, the venous return in the limb to be examined is occluded, for instance, by a method such as shown in FIG. 1. In FIG. 1, an occluding pressure cuff 12, usually employed in sphygmomanometry, is wrapped around the forearm 11 at the side of the heart, in this case, on the upper arm, and inflated to occlude the venous return. The occluding pressure is usually lower than the diastolic blood pressure but higher than the venous pressure and about 40 to 50 mmHg in the case of a healthy subject. Electrodes 13 and 14 are wound around the forearm 11 in its longitudinal direction and electrically connected thereto. An AC signal of 50 KHz, for example, is applied across the electrodes 13 and 14. On the inside of the electrodes 13 and 14, measuring electrodes 15 and 16 are similarly wrapped around the forearm 11 to measure the admittance of the segment between the measuring electrodes 15 and 16. Letting L represent the distance between the measuring electrodes 15 and 16, i.e. the length of the segment to be examined, $\rho$ represent the blood resistivity and $\Delta Y$ represent the difference between the admittance between the measuring electrodes 15 and 16 before venous occlusion and the admittance when the tissue volume of the segment to be examined has been increased by the arterial inflow after venous occlusion, an increase $\Delta V$ in the limb volume by the arterial inflow is expressed as follows:

$$\Delta V = \rho L^2 \Delta Y \tag{1}$$

From this, the blood flow rate F is given as the following time differentiation of the increase $\Delta V$ in the limb volume immediately after venous occlusion:

$$F = \rho L^2 dY/dt \tag{2}$$

Usually the blood flow rate F is normalized to 100 ml of limb volume. Accordingly, a volume change $\Delta V'$ per unit limb volume is given as follows:

$$\Delta V' = \rho L^2 \Delta Y / V_O \tag{3}$$

where $V_O$ is the volume of the limb segment to be examined. The volume change $\Delta V'$ is recorded and the initial gradient of its recorded curve to time or the differentiated value of the volume change $\Delta V'$, that is, the limb blood flow rate per unit limb volume is measured. The reason for such measurement of the limb blood flow rate by recording is that the volume change $\Delta V'$ is very slow and hence is difficult to obtain by differentiation with a calculator circuit.

Figure 2:
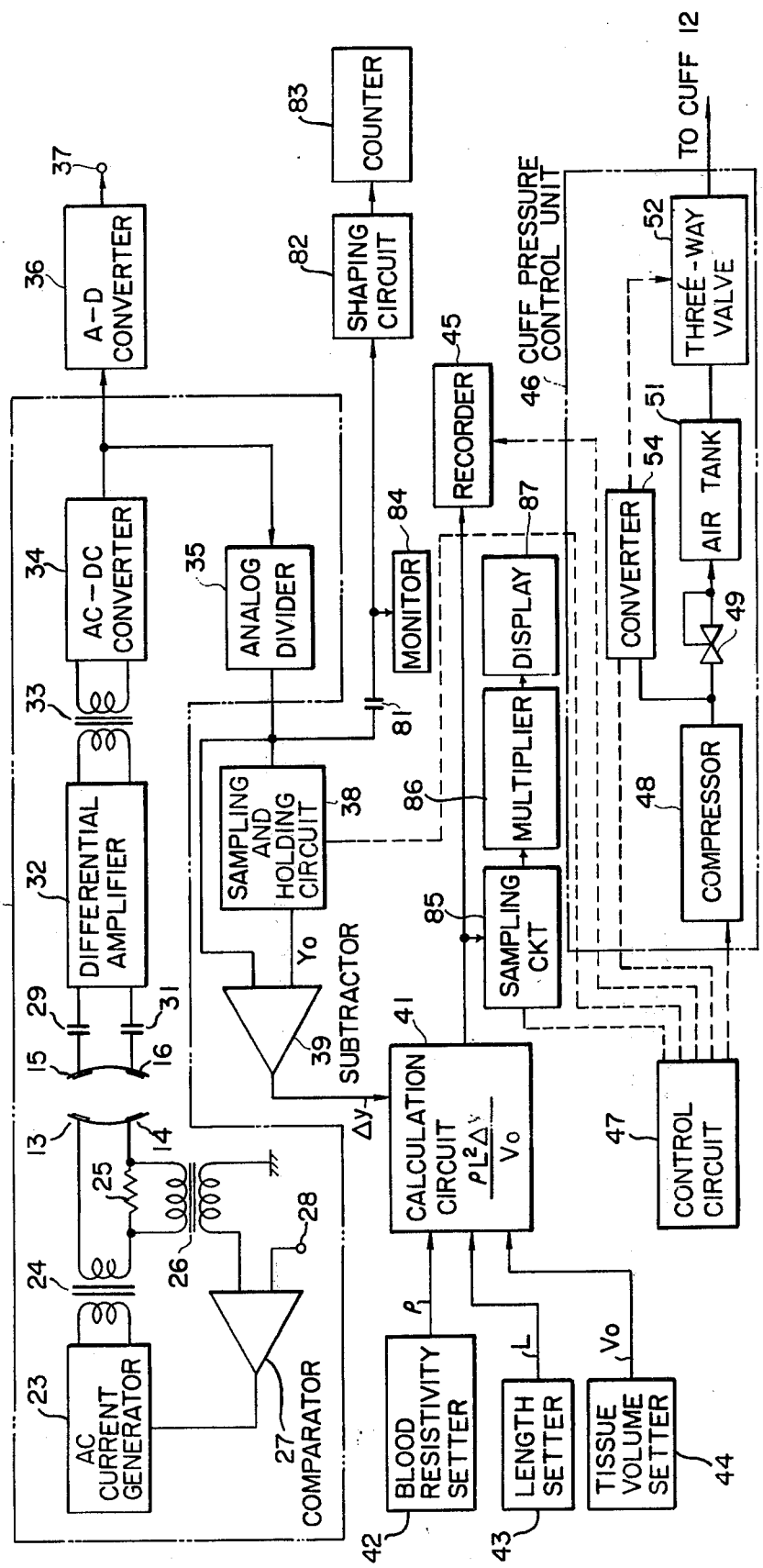
FIG. 2 is a block diagram illustrating an embodiment of the limb blood flow rate of this invention.

In the present invention, the volume change $\Delta V'$ is measured by the employment of such a circuit structure as shown in FIG. 2. In FIG. 2, reference numeral 22 indicates generally an admittance measuring unit, in which an AC current of 1 mA and 50 KHz, generated from an AC current generator 23, for example, is applied across the electrodes 13 and 14, with the common potential point electrically isolated from the AC current generator 23. To this end, the output from the AC current generator 23 is applied across the electrodes 13 and 14 via an isolating transformer 24. The current applying across the electrodes 13 and 14 is maintained accurately at a constant value of 1 mA, for instance. For this purpose, a current detecting resistor 25 is connected in series with the secondary side of the transformer 24 and is connected at both ends to the primary side of a transformer 26. The secondary side of the transformer 26 is grounded at one end and connected at the other end to a comparator 27. In the comparator 27, a voltage detected by the detecting resistor 25 is compared with a reference voltage from a terminal 28, and the compared output from the comparator 27 is negatively fed back to the AC current generator 23 to control it to hold its output current constant.

A signal indicative of the impedance value between the measuring electrodes 15 and 16, that is, a voltage drop based on the abovesaid AC current, is picked up, with the common potential point isolated from these electrodes. In the illustrated embodiment, the above signal is picked up by using a high input impedance lest the AC current should flow in the signal pick-up side to introduce an error in the measured value. To perform this, the measuring electrodes 15 and 16 are respectively connected via coupling capacitors 29 and 31 to a differential amplifier 32 of high input impedance, the output from which is supplied to an AC-DC converter 34 via a common potential point isolating transformer 33. In the converter 34, an AC signal inputted thereto is smoothed after being subjected to full-wave rectification to provide a DC current value corresponding to the impedance between the measuring electrodes 15 and 16. The DC output from the converter 34 is applied to an analog divider 35 to obtain the reciprocal of the DC output; in other words, the DC output is converted to the admittance value between the measuring electrodes 15 and 16. It is also possible to convert the output from the AC-DC converter 34 by an A-D converter 36 into a digital signal and supply it via an output terminal 37 to a display (not shown) for providing a display of the impedance between the measuring electrodes 15 and 16.

The initial value of the admittance measuring unit 22 is retained by a sampling and holding circuit 38 and an initial admittance $V_O$ is stored therein. An admittance value having changed with a variation in the tissue volume of the segment being examined, as a result of venous occlusion, is provided in the analog divider 35, and this admittance value and the initial one $Y_O$ are subtracted from each other in a subtractor 39 to obtain a difference $\Delta Y$ therebetween, which is supplied as an input to a calculation circuit 41.

On the other hand, there are provided a setter 42 for setting the blood resistivity $\rho$, a setter 43 for setting the length L of the segment to be examined and a setter 44 for the limb volume $V_O$ of the segment to be examined. For facilitating the setting of these values, they can be set, for example, by digital switches, and the set values are converted to analog signals for input to the calculation circuit 41. The unit of the blood resistivity $\rho$ is $\Omega \cdot cm$, and resistivities of 50 to 199 $\Omega \cdot cm$ can be set at intervals of 1 $\Omega \cdot cm$, for instance. The blood resistivity varies with the hematocrit value Hct, and the following experimental formula can be employed for the correction of the blood resistivity with respect to the hematocrit value Hct:

$$\rho = 50.7 \exp(0.023 \, Hct)$$

The hematocrit value Hct of an ordinary healthy subject is substantially constant, and the blood resistivity $\rho$ is about 140 $\Omega \cdot cm$. The length L between the measuring electrodes 15 and 16 is measured in cm, and the limb volume $V_O$ between these electrodes is measured in 100 ml.

The set outputs $\rho$, L and $V_O$ from the abovementioned setters 42 through 44 and the output $\Delta Y$ from the subtractor 39 are provided to the calculation circuit 41 for achieving the calculation of the aforesaid formula (3). In this case, for example, $\rho \cdot L^2/V_O$ is calculated first and is then multiplied by $\Delta Y$. The output from the calculation circuit 41 is supplied, for instance, to a heat-pen recorder 45 for recording.

Figure 3:
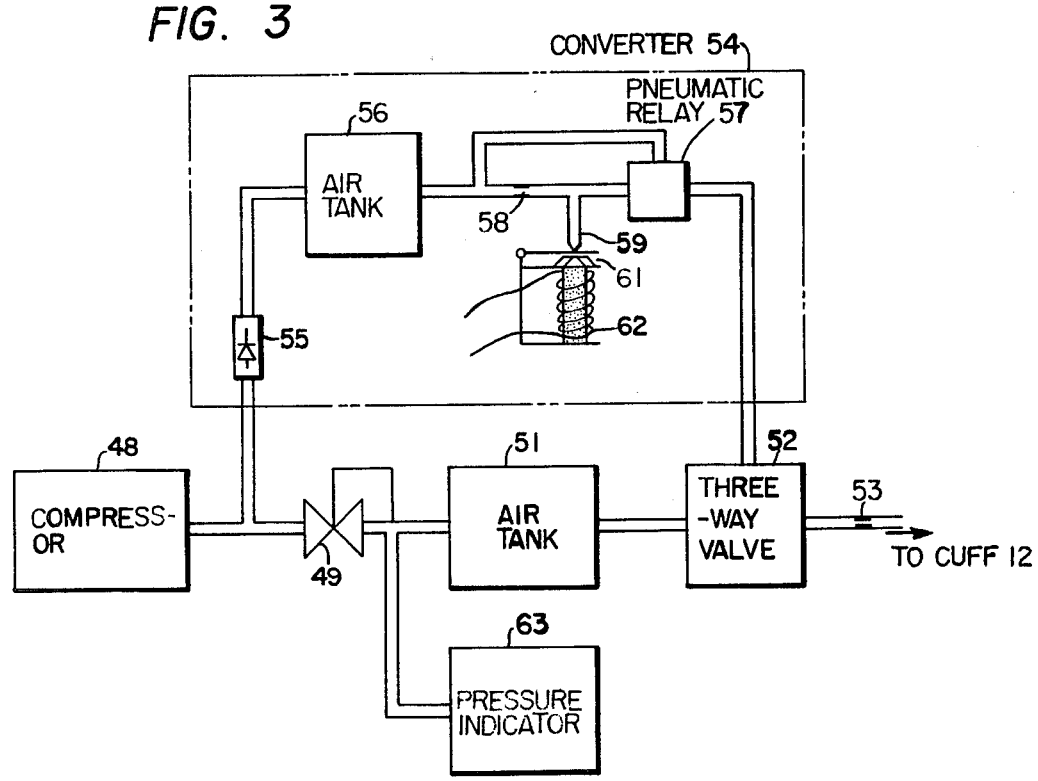
FIG. 3 is a block diagram showing an example of a cuff pressure generating unit utilized in the embodiment of FIG. 2.

A cuff pressure control unit 46 is provided for controlling the pressure to the cuff 12 used for occlusion of the venous return. The cuff pressure, the sampling and holding circuit 38 and the recorder 45 are all controlled by a control circuit 47. The cuff pressure control unit 46 has a construction such, for example, as illustrated in FIG. 3. In FIG. 3, since the control circuit 47 is housed in a casing in close proximity to the calculator circuit and others, an electrical signal for the cuff pressure control is converted to a pneumatic signal so as to prevent the cuff pressure control from generating a large magnetic field which might affect the operations of the other electric circuits. That is to say, compressed air from a small compressor 48 is applied via a precision reducing valve 49 to an air tank 51, from which the air pressure is supplied to the cuff 12 via a three-way valve 52 and a throttle 53. In case of controlling the three-way valve 52 with an electrical signal, an appreciably large electrical signal is required and generates a large magnetic field, as referred to above. To avoid this, a converter 54 is provided for converting an electrical signal to a pneumatic one, and the air pressure from the compressor 48 is branched to be supplied via a fluidic diode 55 to the air tank 56, from which the air provides a pneumatic control signal to the three-way valve 52 via a pneumatic relay 57. On the other hand, the air from the air tank 56 is branched to be supplied via a throttle 58 to a nozzle 59 and the pneumatic relay 57. A flapper 61 is disposed opposite the tip of the nozzle 59 and its position is controlled by an electromagnetic coil 62. Upon energization of the electromagnetic coil 62 to pull the flapper 61 away from the nozzle 59, the three-way valve 52 is controlled by the output from the pneumatic relay 57 to permit the air supply from the air tank 51 to the cuff 12. The pressure of the air tank 51 is indicated by a pressure indicator 63.

Figure 4:
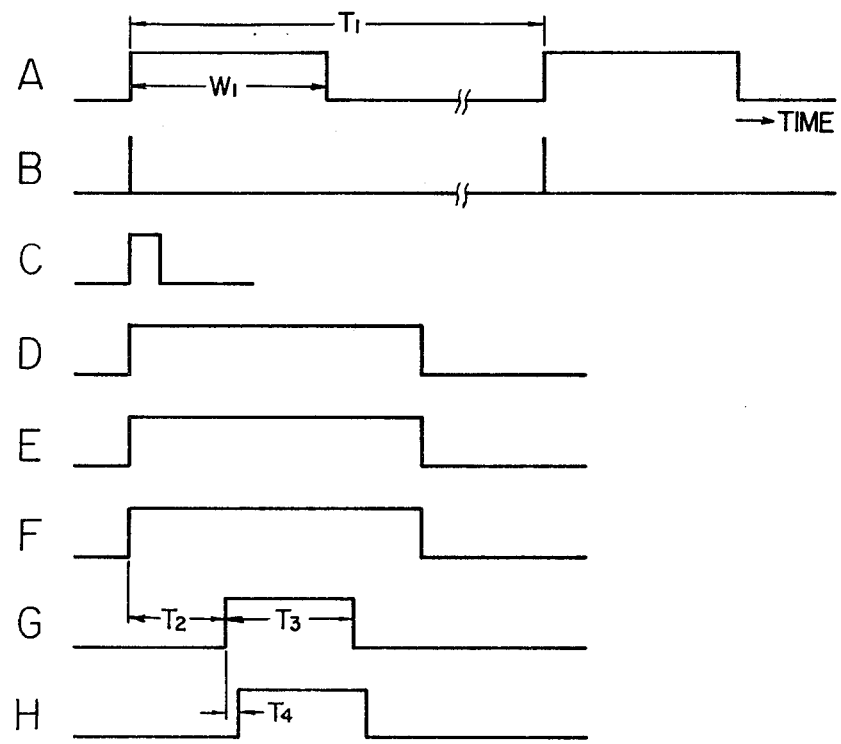
FIGS. 4A to 4H are timing signals showing the sequential control of a logic circuit used in the embodiment of FIG. 2.

The control circuit 47 in FIG. 2 is constructed to perform the operations such, for example, as shown in FIG. 4. That is, a main timer incorporated in the control circuit 47 generates a pulse such as depicted in FIG. 4A which has a period $T_1$ and a pulse width $W_1$. The period $T_1$ can be selected to be for instance, 10 minutes, 30 minutes, an hour or two hours, and the pulse width $W_1$ is selected to be approximately 30 seconds. With the leading edge of the pulse from the main timer, a trigger pulse shown in FIG. 4B is produced, and when required, a pulse for driving a buzzer informing the start of measurement to a subject is generated by the trigger pulse. Further, the trigger pulse is used for driving the small compressor 48 in FIG. 3 and feeding a recording paper of the recorder 45 in FIG. 2 and heating its recording pen, as depicted in FIGS. 4D, E and F, respectively. As shown in FIG. 4G, the electromagnetic coil 62 in FIG. 3 is energized after a period $T_2$, for instance, 10 seconds, to thereby generate the cuff pressure. The cuff pressure is maintained for a period $T_3$, for example, 15 seconds. As illustrated in FIG. 4H, for a period $T_4$, commencing for example, about 1.0 second after the generation of the cuff pressure, the sampling and holding circuit 38 in FIG. 2 samples and holds the output from the divider 35 to retain the initial admittance $Y_O$. For about 15 seconds (a period $T_3$) during which the cuff pressure is applied, the output from the calculator circuit 41 in FIG. 2 is recorded by the recorder 45. Thereafter, the cuff pressure is removed to return the respective parts of the device to their initial state. The period $T_1$ after the abovesaid trigger pulse, a trigger pulse is generated again to achieve the same operations as described above. In the recording, before venous occlusion, the sampling and holding circuit 38 achieves sampling alone and, at this time, the recording pen of the recorder 45 is held to read "zero" and, upon venous occlusion, the sampling and holding circuit 38 is switched to the holding mode of operation to enable recording of only a change in the volume of the limb segment to be examined. The sampling and holding circuit 38 is switched by a timer signal between such modes of operation.

Figure 5:
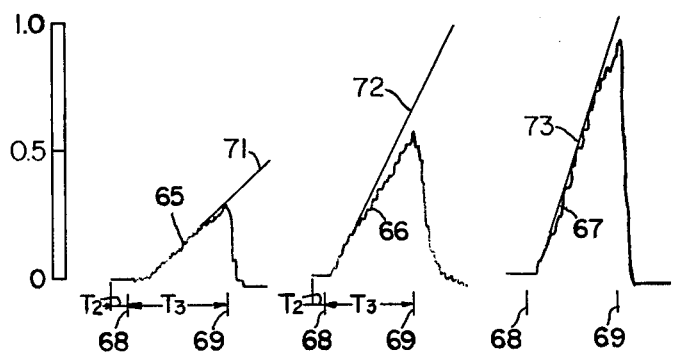
FIG. 5 shows plethysmograms obtained in experiments conducted with the blood flowmeter of this invention.

The recording by the recorder 45 takes such a form as indicated by 65 to 67 in FIG. 5. The start of each of the curves 65 to 67, that is, the left-hand end of each curve in FIG. 5, shows the moment of generation of the trigger pulse. The points indicated by the arrows 68, after the elapse of time $T_2$, each show the moment of application of the cuff pressure. Before the application of the cuff pressure, the recording pen is held to read null and also immediately after the application of the cuff pressure, the recording pen is still maintained at the zero point because the operator output from the calculation circuit undergoes a transient change the instant of application of the cuff pressure. Then, the output from the calculation circuit 41 is recorded. In FIG. 5, the arrow 69 indicates the moment of release of the cuff pressure. The initial gradients of the recorded curves of the calculation results to the time axis (the abscissa), that is, the angles of straight lines 71 to 73 along the rising of the curves 65 to 67 to the lengthwise direction of the recording paper, represent the limb blood flow rates desired to obtain. The illustrated examples were obtained in the case where $\rho = 142$ $\Omega \cdot cm$, $L = 15$ cm and $V_O = 5.25$ 100 ml and the ambient temperature was changed in three ways.

Figure 6:
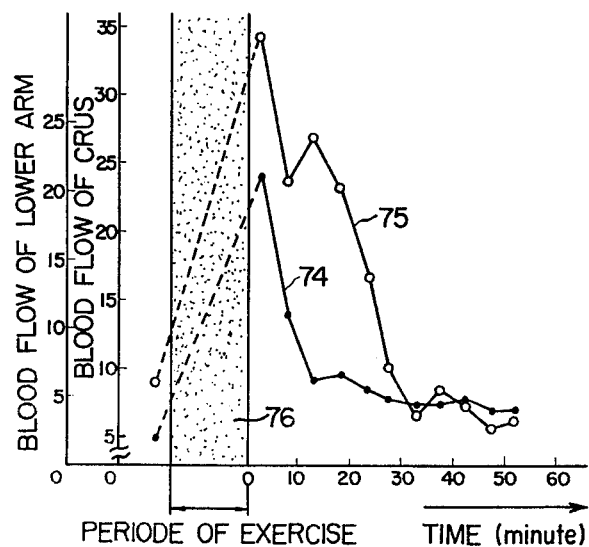
FIG. 6 shows a graphical representation of human limb blood flow variations before and after exercise obtained by the blood flowmeter of this invention.

The blood flow rate is measured in the manner described above. FIG. 6 shows examples of measurement of blood flow variations after exercise in an examinee, the curve 74 indicating the case of the forearm being examined and the curve 75 the case of the calf being examined. The examinee had some exercise for five minutes, as indicated by 76 in FIG. 6. It will be seen from FIG. 6 that the blood flow rate markedly increases immediately after exercise but naturally decreases to return to the state at rest before the exercise as time passes. As referred to previously, this blood flowmeter is capable of automatically monitoring the blood flow rate at regular time intervals $T_1$, but it is also possible to achieve the measurement by generating the trigger pulse at a desired moment. For the calibration of such recording, it is arranged that the output $\Delta V'$ from the computation circuit 41 becomes 0.25 ml/100 ml, for example, when $\rho = 111$ $\Omega \cdot cm$, $L = 15$ cm and $V_O = 999$ ml and $\Delta Y$ ($= 0.1$ mm) is applied to the computation circuit 41. This is in the case where the recording sensitivity is 0.25 m/100 m/FS, and the sensitivity of the recorder 45 is adjusted so that the recorder reaches its full scale under the abovesaid conditions. For such calibration, a calibration box is incorporated in the blood flowmeter, which box sets resistance values, for instance, 0 to 200Ω at intervals of 10Ω and is capable of changing each resistance value by 0.1Ω and 1Ω. Various values of ΔY are produced with the calibration box and applied as the reference values of ΔY to the computation circuit 41 for the abovesaid calibration. By picking up the AC components in the output from the divider 35 or the subtractor 39, arterial ripples are measured. For example, in FIG. 2, the output from the analog divider 38 is branched by a capacitor 81, and only the AC components are picked up. The AC components are shaped by a wave-form shaping circuit 82 into shaped pulses, which are counted by a counter 83 for unit time. The count value of the counter 83 is indicative of the heart rate. Such simultaneous measurement of the heart rate with the blood flow rate enables an analysis of their relationship to each other.

On top of that, the blood flowmeter of this invention can be employed for sphygmomanometry. In the measurement of the blood flow rate the cuff pressure is selected, for instance, about 50 mmHg to occlude the venous return alone, but in the measurement of blood pressure the cuff pressure is further raised to occlude the arterial inflow as well as the venous return. Upon occlusion of the arterial inflow, the cuff pressure is gradually reduced, and the generation of the arterial inflow is detected in the form of generation of a ripple, for instance, by means of a monitor 84 connected to the input side of the waveform shaping circuit 82, and then the systolic blood pressure is measured from the cuff pressure at which the arterial inflow is permitted. The cuff pressure is further lowered, and restoration of the arterial inflow to its steady state is detected from the amplitude of the ripple having become constant in the monitor 82, and then the diastolic blood pressure is measured from the cuff pressure at that time. It is also possible that the cuff pressure at which the ripple disappears as a result of raising the cuff pressure is used as the systolic blood pressure.

The blood flow rate is obtained by recording with the recorder but may also be obtained in the following manner: For instance, in FIG. 2, the output level of the calculation circuit 41 is sampled by a circuit 85 under an instruction from the control circuit 47 $T_5$ seconds after the application of the cuff pressure, and the sampled output is multiplied by $60/T_5$ in a circuit 86 to be converted into the blood flow rate per minute, thereafter being displayed in a digital or analog form on a display 87.

As has been described in the foregoing, it is possible with the limb blood flowmeter to measure the limb blood flow non-invasively and successively. On top of that, since the measured output bears no relationship to the initial admittance, as expressed by the formula (3), the measured value excludes the electrical characteristics of tissues outside of the object to be examined, and hence is accurate. Further, the blood flowmeter of this invention can be easily used without any danger to examinees and is also convenient for measuring the limb blod flow rates of many persons. As described previously with regard to FIG. 2, an AC signal is applied to the limb to be examined, but since the measuring device and the common potential are isolated by the transformers 24, 26 and 33 from each other, there is no possibility of the limb receiving an electrical shock. The measuring electrodes 15 and 16 are connected via capacitors to the input side of a differential amplifier, so that a circuit of high input impedance can be connected to the electrodes 15 and 16. For example, in the case of connecting the isolating transformer 33 directly between the electrodes 15 and 16, even if a high input impedance transformer is employed, its input impedance becomes appreciably low to introduce an error in measurement, but the abovesaid embodiment is free from such a defect and ensures highly accurate measurement.

The current applying across the electrodes 13 and 14 is detected by the resistor 25 and controlled by the detected output to remain constant, and this also assures measurement of high accuracy. For instance, even if the AC signal generator 23 itself is so constructed as to provide a constant current output, a constant AC current cannot always be produced due to a change in the contact resistance between the electrodes 13 and 14 and the limb 11 being examined, but the circuit structure shown in FIG. 2 ensures to accurately provide a constant current. While the foregoing has described the blood flowmeter of this invention in connection with the case where the impedance components are measured and then the admittance is obtained by way of division, it is also possible to design the blood flowmeter to directly measure the admittance. In such a case, a method of voltage clamp is available to the limb to be examined in place of the method of current clamp.

It will be apparent that many modifications and variations may be affected without departing from the scope of the novel concepts of this invention.

What is claimed is:
1. A limb blood flowmeter comprising:
   occluding pressure means for applying pressure to a limb to be examined on the side of the heart to occlude only the venous return;
   admittance measuring means for measuring the admittance of the limb;
   means for holding an initial admittance of the limb at the start of measurement;
   a subtractor for deriving an admittance change ΔY from the difference tetween the initial admittance and an admittance measured subsequently and operative to produce an electrical signal corresponding to ΔY;
   means for setting the value of the blood resistivity ρ of the limb and operative to produce a corresponding electrical signal;
   means for setting the value of the length L of the region of the limb to be examined and operative to produce a corresponding electrical signal;
   means for setting the value of the tissue volume $V_O$ of the region to be examined and operative to produce a corresponding electrical signal;
   a calculator responsive to said electrical signals for calculating $\rho L^2 \Delta Y/V_O$ based on the output ΔY from the subtractor and the blood resistivity ρ, the length L and the volume $V_O$ set in the setting means; and
   a controller for controlling the occluding pressure means and the holding of the initial admittance of the limb.

2. A limb blood flowmeter according to claim 1, wherein the admittance measuring means is composed of impedance measuring means for measuring the impedance of the limb and a divider for obtaining the reciprocal of the measured impedance.

3. A limb blood flowmeter according to claim 2, wherein the impedance measuring means is composed of first and second electrodes disposed on the limb at spaced positions in the longitudinal direction of the limb, AC current supply means for applying a substantially constant AC current across the first and second electrodes, third and fourth electrodes disposed on the limb on the inside of the arrangement of the first and second electrodes, and impedance signal detecting means for obtaining a voltage corresponding to the impedance between the third and fourth electrodes.

4. A limb blood flowmeter according to claim 3, wherein the AC current supply means is composed of an AC current generator, an isolating transformer for applying the AC current from the AC current generator across the first and second electrodes, a current detecting resistor connected in series with the secondary side of the isolating transformer to provide a voltage proportional to the magnitude of the applied AC current, a transformer having its primary side connected to both ends of the current detecting resistor, and a comparator for comparing a voltage produced at the secondary side of the transformer with a reference voltage to control the AC current generator by negative feedback to make constant the current flowing across the first and second electrodes.

5. A limb blood flowmeter according to claim 3, wherein the impedance signal detecting means is composed of first and second coupling capacitors respectively connected at one end to the third and fourth electrodes, a differential amplifier connected between the other ends of the first and second coupling capacitors, a transformer connected to the output side of the differential amplifier, and an AC-DC converter connected to the secondary side of the transformer.

6. A limb blood flowmeter according to claim 1, wherein the calculator is composed of a part for calculating $\rho L^2 / V_O$ and a part for multiplying the calculated result by $\Delta Y$.

7. A limb blood flowmeter according to claim 1, wherein the occluding pressure means is composed of a band-like bag wrapped around the limb on the side of the heart and supplied with pressurized air to be inflated, and a pressure control part for controlling the supply of the pressurized air.

8. A limb blood flowmeter according to claim 7, wherein the pressure control part is composed of a compressed air source, means for converting a pressure control electrical signal from the controller to a pneumatic signal, and a three-way valve controlled by the converted pneumatic signal to switchingly connect the band-like bag to the compressed air source and the outside air.

9. A limb blood flowmeter according to claim 1, which further includes a recorder supplied with the output from the calculator to record it.

10. A limb blood flowmeter according to claim 1, which further includes a circuit for sampling the output from the calculator $T_5$ seconds after the occlusion of the venous return, a circuit for multiplying the sampled value by $60/T_5$, and a display for displaying the multiplied result.

11. A limb blood flowmeter according to claim 1, which further includes means for picking up AC components of the measured admittance from the admittance measuring means, means for counting pulses of the AC components every unit time, and means for displaying the counted result as the heart rate.

12. A limb blood flowmeter according to claim 1, wherein the occluding pressure means is so constructed as to provide a pressure for also occluding the arterial inflow in the limb, and which further includes means for detecting the magnitude of the arterial inflow in the limb, means for displaying, as the systolic blood pressure, the pressure of the occluding pressure means upon stoppage or starting of the arterial inflow by pressure increasing or decreasing control of the occluding pressure means, and means for displaying, as the diastolic blood pressure, the pressure of the occluding pressure means at the moment of the amplitude of the arterial inflow becoming constant when the occluding pressure means is switched from its pressure increasing state to its pressure decreasing state.

13. A limb blood flow rate measuring method comprising the steps of:
   appling pressure to a limb to be examined on the side of the heart to occlude only the venous return;
   measuring the admittance of the limb and holding the initial admittance of the limb at the start of measurement;
   measuring the admittance of the limb after holding of the initial admittance and subtracting the measured value from the initial admittance to obtain an admittance change $\Delta Y$;
   calculating $\Delta V = \rho L^2 \Delta Y / V_O$ based on the blood resistivity $\rho$ of the limb to be measured and the length L and the tissue volume $V_O$ of the region of the limb to be examined; and
   obtaining the limb blood flow rate from an initial gradient of the calculated $\Delta V$.

* * * * *